(12) United States Patent
Meissner et al.

(10) Patent No.: US 9,760,678 B2
(45) Date of Patent: Sep. 12, 2017

(54) SYSTEMS AND METHODS IN DIGITAL PATHOLOGY

(76) Inventors: Michael Meissner, Pittsburgh, PA (US); Ronald Stone, Pittsburgh, PA (US); Raghavan Venugopal, Pittsburgh, PA (US)

( * ) Notice: Subject to any disclaimer, the term of this patent is extended or adjusted under 35 U.S.C. 154(b) by 550 days.

(21) Appl. No.: 14/235,179

(22) PCT Filed: Jul. 27, 2012

(86) PCT No.: PCT/US2012/048731
§ 371 (c)(1),
(2), (4) Date: May 5, 2014

(87) PCT Pub. No.: WO2013/016715
PCT Pub. Date: Jan. 31, 2013

(65) Prior Publication Data
US 2014/0257857 A1    Sep. 11, 2014

Related U.S. Application Data

(60) Provisional application No. 61/512,341, filed on Jul. 27, 2011.

(51) Int. Cl.
*G06F 19/00* (2011.01)
*A61B 5/00* (2006.01)
*G06Q 50/24* (2012.01)

(52) U.S. Cl.
CPC ............ *G06F 19/321* (2013.01); *A61B 5/743* (2013.01); *G06F 19/32* (2013.01); *G06F 19/3406* (2013.01); *G06Q 50/24* (2013.01); *A61B 5/4381* (2013.01); *A61B 2576/00* (2013.01)

(58) Field of Classification Search
CPC ................. G06F 19/321; G06T 7/0012; G06T 2207/10056; G06T 2210/41; G06K 9/0014; A61B 10/00
See application file for complete search history.

(56) References Cited

U.S. PATENT DOCUMENTS

| | | | |
|---|---|---|---|
| 2002/0118223 A1* | 8/2002 | Steichen | G06F 3/033 715/745 |
| 2002/0169735 A1* | 11/2002 | Kil | G06F 17/30539 706/46 |
| 2006/0146071 A1 | 7/2006 | Morita et al. | |
| 2006/0195484 A1 | 8/2006 | Mahesh | |
| 2007/0030529 A1* | 2/2007 | Eichhorn | G06K 9/46 358/453 |
| 2007/0140536 A1 | 6/2007 | Sehnert et al. | |
| 2008/0120142 A1* | 5/2008 | Jakobovits | G06Q 50/24 705/3 |
| 2009/0132916 A1 | 5/2009 | Filatov | |
| 2009/0138318 A1 | 5/2009 | Hawkins et al. | |
| 2009/0276392 A1 | 11/2009 | Yan | |

(Continued)

*Primary Examiner* — Michelle L Le
(74) *Attorney, Agent, or Firm* — Ronald Law Group, LLC

(57) ABSTRACT

A system and method of increasing digital pathology productivity is provided. The system accepts case information from a plurality of sources and pre-processes that information in order to present the slides in an order and orientation dictated by preference and/or reviewing standard. Upon application of the system and method, the appearance and behavior of the user interface is optimized for the user.

12 Claims, 22 Drawing Sheets

(56) References Cited

U.S. PATENT DOCUMENTS

| | | | |
|---|---|---|---|
| 2010/0023857 A1* | 1/2010 | Mahesh | G06F 3/016 715/701 |
| 2010/0131482 A1 | 5/2010 | Linthicum | |
| 2010/0211409 A1 | 8/2010 | Kotula | |
| 2010/0290678 A1 | 11/2010 | Dekel | |
| 2011/0060766 A1* | 3/2011 | Ehlke | G06F 3/0481 707/802 |
| 2011/0128367 A1 | 6/2011 | Yoshioka | |

* cited by examiner

Example – Kidney (cancer near margins)

- Detect if tumors extend beyond margins } Tool (visual) + opt. Tool (auto-highlight)

Example – Skin (melanoma)

- Always align horizontally
- Always review at 5X (default)
- Provide melanoma seed tool
  (auto-segment + auto-measure)

Hanging Protocol + New Tool
(check mark in Configuration App)

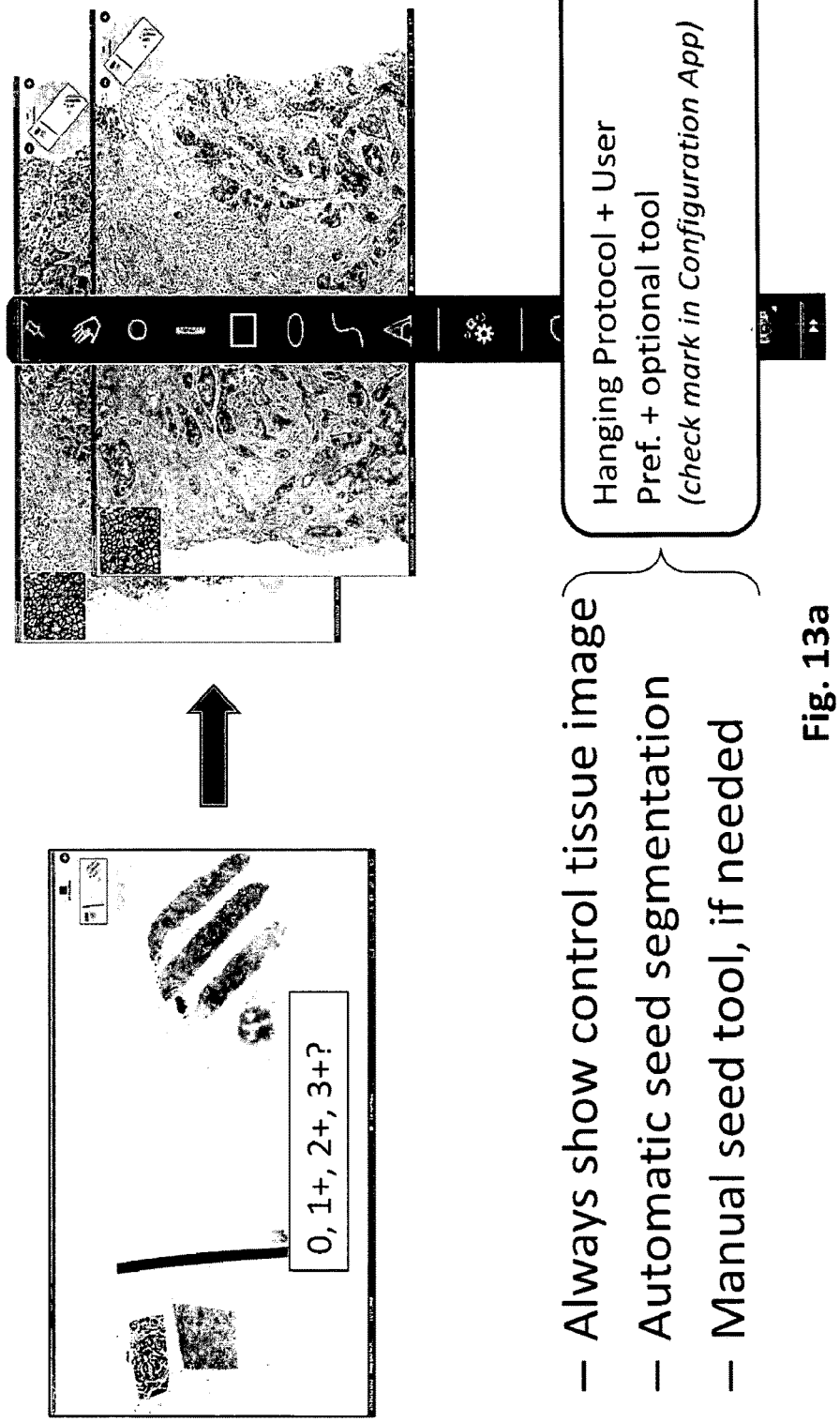

Example – Breast Biopsy (basic)

- Always align vertically
- Always review at 10X (default)
- Start with H&E slide
- Start top of left-most biopsy Hanging Protocol + User Pref.
*(check mark in Configuration App)*

SYSTEMS AND METHODS IN DIGITAL PATHOLOGY

CROSS-REFERENCE TO RELATED APPLICATION

This patent application is an international application and claims priority to provisional U.S. Patent Application Ser. No. 61/512,341, filed Jul. 27, 2011, and entitled "Systems and Methods in Digital Pathology", the entire specification of which is incorporated by reference herein.

FIELD OF THE INVENTION

This invention generally relates to systems and methods for context and purpose driven interaction in digital pathology. More particularly, the invention relates to systems and methods for interfacing applications and/or systems, which provide for customized graphical user interfaces in the field of digital pathology.

BACKGROUND OF THE INVENTION

Diagnostic methods in pathology carry out the detection, identification, quantization, and characterization of cells, structures, and other items of interest. In the past, either a lab technician or a pathologist has typically performed examination of biological tissues manually. In the manual method, a slide prepared with a biological sample is viewed at a low magnification under a microscope to visually locate candidate cells of interest. Those areas of the slide where cells of interest are located are then viewed at a higher magnification to confirm those objects as cells of interest, such as tumor or cancer cells. Such a process is not only cumbersome, but time consuming.

This manual process performed by pathologists has improved with the use of digital images, i.e. photographed or scanned images of slides containing stained biological samples that have been digitized. High-resolution digital images of a biological sample are typically obtained using a microscope and specialized imaging hardware. However, the use of these digital images can lead to inefficiencies in reviewing the samples. For example, a whole-slide image (WSI) of a typical breast core biopsy is usually very large, and has 'n' number of tissues on the same slide in a random orientation. When a pathologist reviews this case, they spend considerable amounts of time first in the manual rotation of the slide to a preferred orientation, followed by the challenge of using the mouse to pan the image at the highest magnification from one tissue to the next. Not only is this process of viewing the images inefficient due to the inability to view images according to a preferred view, or modify the appearance and/or behavior of the view, but it also limits the number of cases that can be read in one day. Accordingly, there is a need for a more efficient system and method that provides a customizable user interface to a pathologist for interacting with digital pathology images.

SUMMARY OF THE INVENTION

An aspect of the present invention is a system and/or method that provides a customized user interface for interaction with digital pathology images. The method includes acquiring data, wherein the data comprises at least one digital image, processing the data based on case information, for example, and providing a customized user graphical interface resulting from said processing.

These and other aspects of the present invention will be more apparent from the following description.

BRIEF DESCRIPTION OF THE DRAWINGS

FIG. 13a demonstrates a user interface view of the Readflow™ illustrated in FIG. 13.

Figure 1:
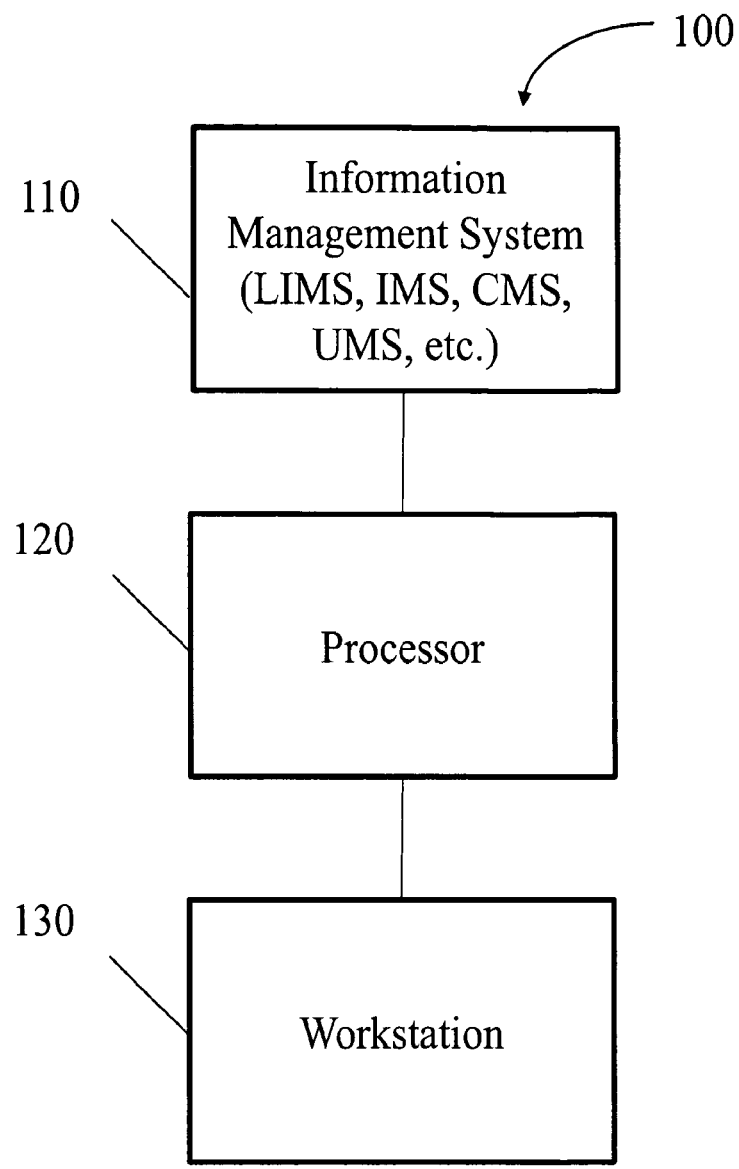
FIG. 1 illustrates an exemplary system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

As used herein, "case information" includes any information relating to the case, including, but not limited to, patient name, birth date, age, gender, type of case, type of procedure, number of images, bench and stain types, patient admission date, DICOM header fields and the like.

As used herein, "digital image" includes, but is not limited to, photographed or scanned slides of biological samples, including whole slide images (WSI) and the like.

As used herein, "information management system" may be a digital library or database, such as a repository or the like as appreciated by those skilled in the art. The information management system may include one or more of a user management system, a case or context management system, an image management system, a rules management system, a laboratory information management system (LIS), an electronic medical record (EMR) and/or any other management system as appreciated by one skilled in the art. The image management system may include at least digital images. The case or context management system may include at least case information. The user management system may include information about a user's preferences such as preferences for viewing order of images, orientation of the WSI, the magnification of the WSI, tool options that can be initiated, and the like, as appreciated by one skilled in the art. For example, the preferences may be specific to a lab technician or doctor. Alternatively, the preferences may be specific to a health institution or laboratory facility.

As used herein, "user interface", refers to the interface that allows the user, for example end users such as pathologists, to input commands and data and receive results, such as a graphical user interface (GUI). The terms "user interface" and "graphical user interface" are used interchangeably herein.

As used herein, "workstation" includes any computer, display device, monitor, and the like as appreciated by one skilled in the art.

In various aspects, the invention is directed to systems and methods for interfacing applications and/or systems which provide customized graphical user interface(s) in the field of digital pathology. In particular, the systems and methods of the invention allow for context and purpose driven interaction in digital pathology. As described in further detail herein, in an embodiment, the invention allows for the processing of data and images from an information management system in conjunction with the needs or preferences of a pathologist to produce a customized user graphical interface which, for example, optimizes appearance and/or behavior of the graphical user interface(s). The customized graphical user interface (the "Readflow™") allows for efficient work flow by pathologists of the case and/or the digital image. As described further herein, the systems and methods of the invention utilize a processor that processes data relating to the type of case or panel being reviewed and the known needs or preferences of the user.

In an embodiment of the invention, the method includes acquiring data including at least one digital pathology image, processing the data, utilizing the processed data to provide a customized graphical user interface. The customized graphical user interface may be customized based on the case information related to at least one digital pathology image, for example, the type of case such as breast, cancer, skin, or other. The graphical user interface may also be customized based on an end-user's preferences, such as, for example, magnification, orientation of specific image, addition of tools, or other. In an aspect of the invention, the customized graphical user interface provides an interactive environment in which the end user may interact with at least one digital image. The environment may include changes to appearance and/or behavior of the user graphical interface.

In embodiments, the acquired data includes at least one digital pathology image. The acquired data may also include a set of digital images. The set of digital images may be grouped according to, for example, a patient or a case procedure. Alternatively, the acquired data may include at least one digital image and any other desired information such as associated case information. In other embodiments, the acquired data may include at least one digital image and user preferences. In even further embodiments, the acquired data may include information from a medical pathology atlas to impact appearance and/or behavior of the graphical user interface.

In another aspect of the invention, the method includes acquiring data including a digital image, wherein the digital image has associated case information, processing the data based on the case information, and utilizing the processed data to provide a customized graphical user interface.

The method of the invention may be performed by an exemplary system as illustrated in FIG. 1. The system 100 in FIG. 1 includes at least one information management system 110, a processor 120 for running the software that makes up the information management system, and a workstation 130 including a display device such as a monitor or other screen for displaying a graphical user interface to a user, a mouse or other means of identifying certain elements on the screen and keyboard or other means of entering information, for example, into the at least one information management system 110. The at least one information management system 110, processor 120 and workstation 130 are in operable communication with each other in any manner as appreciated by one skilled in the art. Additionally, as is readily appreciated by those skilled in the art, the customized user interface according to the invention can be used in combination with any system having a processor and display.

The at least one information management system 110 includes at least a digital image and associated case information. The case information and the corresponding digital image may be obtained from a single management system or multiple data management systems. In embodiments using a single management system, the case information may be associated with the digital image on the digital image itself, such as through a tag, DICOM header, etc. In other embodiments where multiple management systems are utilized, the case information may be located in a case information management system and the digital images may be separately located in an image management system. In such a case, the case information management system and the image management system are in operable communication with each other as appreciated by one skilled in the art such that the case information may be correlated or associated with the corresponding digital image. In an embodiment, data fields such as patient identification can be used as a means for locating and correlating the case information with the corresponding digital image.

The at least one management system 110 then communicates at least the digital image and case type or procedure type to the processor 120. The processor 120 may be any machine that receives and processes information as appreciated by one skilled in the art. For example, the processor 120 may be a central processing unit (CPU), microprocessor, graphics processing unit (GPU) and the like. In embodiments, the processor 120 may be programmed to implement a rules engine. The rules engine may have programmed thereon predefined rules such that it evaluates incoming information based on one or more predefined rules. In embodiments, the rules engine may include a predefined set of rules determined or set forth in guidelines of governing bodies. In embodiments, the rules engine may include a set of predefined rules for each case type (e.g. hanging protocol for breast, prostate, kidney, etc.) as well as predefined rules based on tests performed for each case type (e.g. H&E stain type, procedure type, etc.). Additionally, the rules engines may include predefined rules based on an individual user's preference, or alternatively, an institution's preferences. In embodiments, multiple predefined sets of rules can be used concurrently. For example, a rule set used for a skin case may be used in conjunction with a predefined set of rules for a specific user's preference. In an alternative embodiment, the rules engine may learn an end user's desired preferences and/or needs based on previous behaviors of the user, as appreciated by one skilled in the art.

In various embodiments, after evaluation of the acquired data or information by the rules engine, the processor 120 executes the determined actions by the rules engine. The processor may process the acquired data or information for example, by running an algorithm on the received information (e.g. scanning the digitized images for areas of probable mitotic activity in order to present them to the pathologist in an automated way). Alternatively, the rules engine may result in a determination that no algorithm needs to be performed on the data in which case no further action is taken by the processor. In embodiments, the processor 120 may process the data a number of times, such as running multiple algorithms on the same information sequentially. Preferably, the acquired data may be continually processed until a determination is made by the rules engine that no further processing remains to be performed on the acquired data.

The processed data from the processor 120 is then utilized to provide a customized graphical user interface on workstation 130 for the pathologist to interface with. For example, the processed data may result in the modification of the appearance of the application and/or modification of the behavior of the application. Appearance modification may include, for example, change in orientation, magnification of an image or a portion of an image, change in display area and the like. Behavior modification may include for example, tools that by themselves could change appearance of the application or change existing as well add new behaviors to the application. For example, in a breast panel IHC, the user may manually outline a region of interest on an image, which then is automatically identified by the system 100 on corresponding images. In embodiments, the tools available to the pathologist for manipulation of a particular image may be selected based on user preferences to provide a customized graphical user interface for the pathologist to interact with the digital image(s).

The various Readflows™ and data processing described herein may be implemented in software running on computers, servers or other processing systems. In use, the software for providing a customized graphical user interface may be launched when the pathologist interacts with the workstation 130 such as by moving the mouse, using the keypad, clicking on an icon or the like. Once launched, the user clicks on the desired case and upon doing so will be presented with an interface that has been customized based on, for example, the type of image and/or case information.

In embodiments, the systems may include more than one workstation, management information system and/or processors. For example, the system may include multiple servers, such as an individual server that maintains user preferences and/or images. The workstation 130 may be capable of communicating with the at least one information management system 110 and/or the processor 120. The workstation, information management system and processor can communicate electronically over a wired or wireless communication, for example. Additionally, the processor 120 may be located in any component of the system 100. For example, the processor 120 may be located within the workstation 130 or the at least one information management system 110 and is in operable communication with a workstation. This results in providing a customized user interface as appreciated by one skilled in the art.

In embodiments, the processor 120 may communicate with a separate server retaining the information management system that includes, for example, a digital library of whole slide images. The servers, such as the at least one information management system 110 and/or processor 120 may reside at the same location or at different locations. For example, the servers may reside onsite at the pathologist's office or alternatively, remotely such as off-site at a medical institution. In other embodiments, the system may include more than one processor.

The system 100 may further include an imaging modality such as a scanner, or the like, to capture the image data in a digital format. For example, when a pathology slide is obtained, a user may scan the image and place the image automatically in the digital image library or, for example, image management system. Alternatively, the image may be scanned and manually moved from a separate server or workstation to the digital archive.

In yet other embodiments, the system may include a scanner, software, and medical imaging devices for electronic capture, viewing, analysis, storage and retrieval of digital images of pathology slides and specimens; software for clinical information and workflow management for pathologists, and/or image analysis software that uses algorithms.

Figure 2:
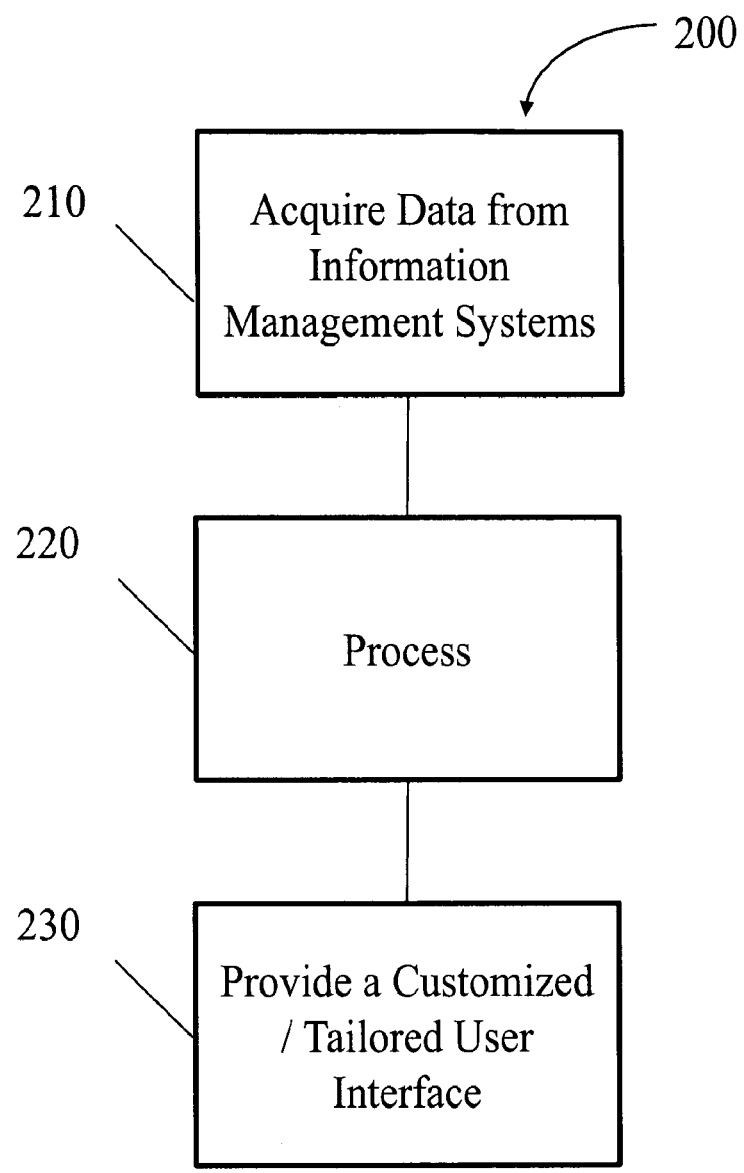
FIG. 2 illustrates a method according to another embodiment of the present invention.

Another aspect of the invention is directed to methods of creating a Readflow™ for a user such as a pathologist. FIG. 2 illustrates a method of the invention 200 where data is acquired from the at least one information management system 210, the data is then processed by the processor 220 and the processed data results in a customized user interface 230. In further detail, the method may include acquiring digital images from an image management system and data such as patient information and case type and/or procedure type from the context management system. The acquisition of data may occur sequentially in any order or may occur simultaneously. The processor, which may be on a separate server, evaluates the data through a rules engine and may process the data for example, by running an algorithm(s) on the data. The processed data results in a modification or change of appearance and/or behavior of the graphical user interface. As such, a digital image is then displayed on a workstation via a graphical user interface in a customized and interactive manner based on behavior and application.

As discussed above, the method may be initiated by the end user interacting with the workstation 130. In this embodiment, the data is available in the at least one management system prior to the user's interaction with the workstation and may be simultaneously processed upon the user's interaction with the workstation.

Figure 3:
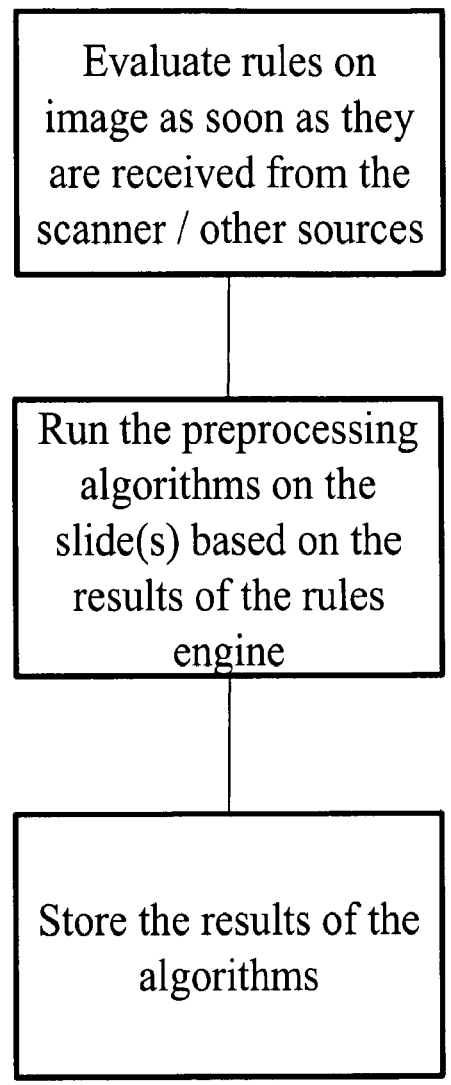
FIG. 3 illustrates a method according to another embodiment of the present invention.

In other embodiments, the data may be pre-processed as illustrated in FIG. 3 through a processor such as a pre-processing engine. The pre-processing engine may have additional and/or a different set of rules than on the rules engine of processor 120. In embodiments, the pre-processing engine may have its own rule engine. The input for the pre-processing engine may be a scan recently acquired from the scanner or from another source. The pre-processing engine processes the recently acquired image based on its set of rules and for example may utilize different algorithms than that of processor 120. The results of these algorithms may be stored anywhere on system 100, such as in the case management system (CMS). The pre-processing of the data therefore allows for processing of data that may, for example, take a longer period of time, prior to any end user interface with the workstation 130. For example, when the user subsequently views this slide or this case, the appropriate graphical user interface and/or data is readily available for display to the end user based on the pre-processing results, data and other information.

Examples of case types/procedure types that would undergo pre-processing include case types/procedure types that require longer processing times than normal. The pre-processing engine thus allows for processing of the data prior to the end user's interaction with the workstation/graphical user interface. An example of a case type that may undergo pre-processing is Mitosis counting/Mitosis identification that is processed by the respective algorithm of the applicable Readflow™. In this example, mitosis may be present anywhere in the WSI and results in difficulty in processing the entire slide on the client side when the pathologists open the case/slide. The pre-processing engine will use the rules engine to determine if a slide needs to be processed for Mitosis. It will then process the images and then store the resulting output data (area where Mitosis could be present). When the pathologists open the particular slide/case, this additional data is then displayed and drives the appearance and behavior of the graphical user interface to the user along with the tools to navigate between the different regions in the image where Mitosis could be present.

The pre-processing may also be used for any Readflow™ that needs co-registration, for example, to determine how to register "n" number of slides, which happen to be different slices of the same sample, for example. This information may be stored after the pre-processing step and may be used to setup the graphical user interface when the pathologists open a particular Readflow™ that uses co-registration. Examples of such Readflows™ include Breast panel (H&E, IHC), breast biopsy and hotspots as discussed below.

Another aspect of the invention includes the Readflows™ for each case type and/or case panel as further described below. As discussed above, the Readflows™ allow for the appearance, behavior, or both the appearance and behavior of the graphical user interface to change based on, for example, the case information and user preferences/needs. Examples of Readflows™ discussed below that change the appearance of the original digital image include, but are not limited to the Gleason Score, GU (prostate tumor and hyaline), GU (kidney, cancer), skin (melanoma, epidermis), breast biopsy, H&E and IHC, and core, tissue jumper and hotspots. Examples of Readflows™ discussed below that change appearance and behavior include, but are not limited to, the following: skin (melanoma, epidermis), and breast (H&E, IHC, biopsy and core). Examples of Readflows™ that include data subject to pre-processing include, but are not limited to, breast (H&E, IHC) and biopsy and hotspots.

The Readflows™ described herein are not to be all-inclusive and/or limiting and may be combined with each other and/or built on to produce additional Readflows™. The following examples are exemplary Readflows™ of the invention.

Gleason Score Readflow™

Figure 4:
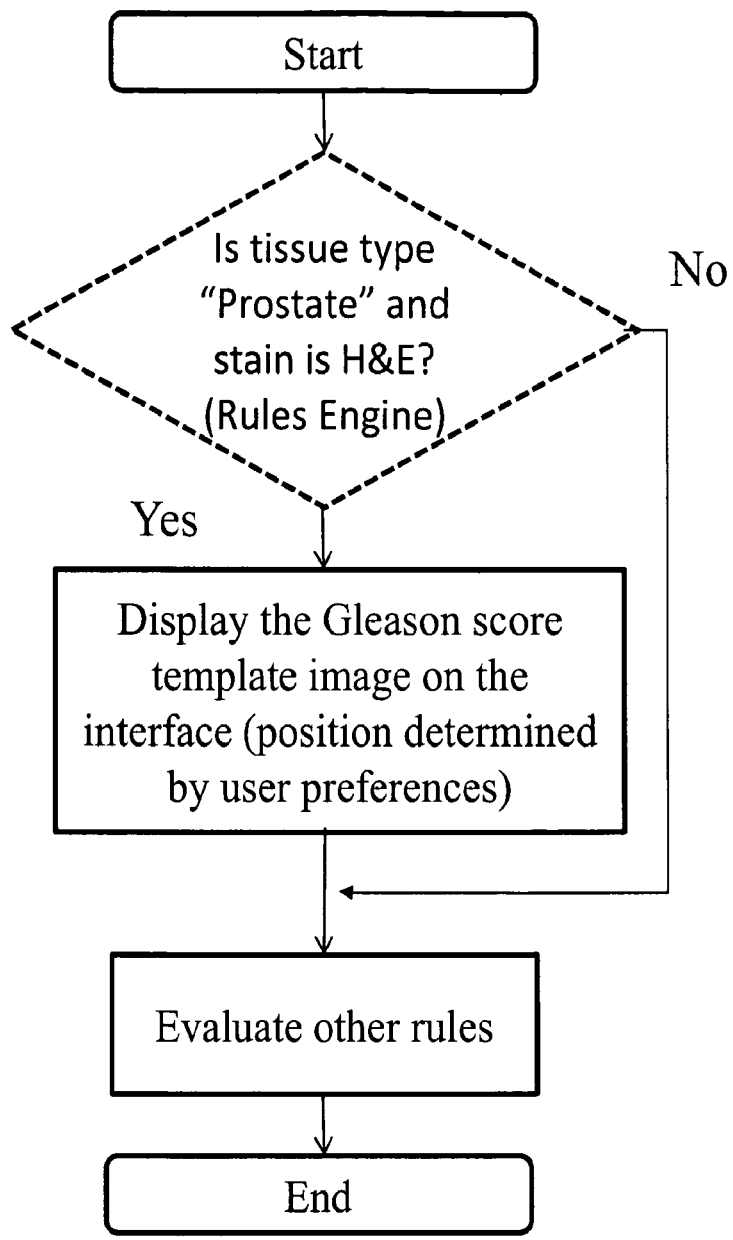
FIG. 4 illustrates a Readflow™ for GU (Gleason score template) in accordance to an embodiment of the present invention.

Referring, now, to FIG. 4, Gleason scores are needed for grading prostate cancer. Typically, pathologists will access a reference source to review the grading patterns for determining Gleason scores. In this Readflow™, if the rules engine determines from the case information or some other source that the case is "prostate", it automatically displays the Gleason score template on the user interface without any prompting or action from the user.

GU (Prostate Tumor Area) Readflow™

Figure 5:
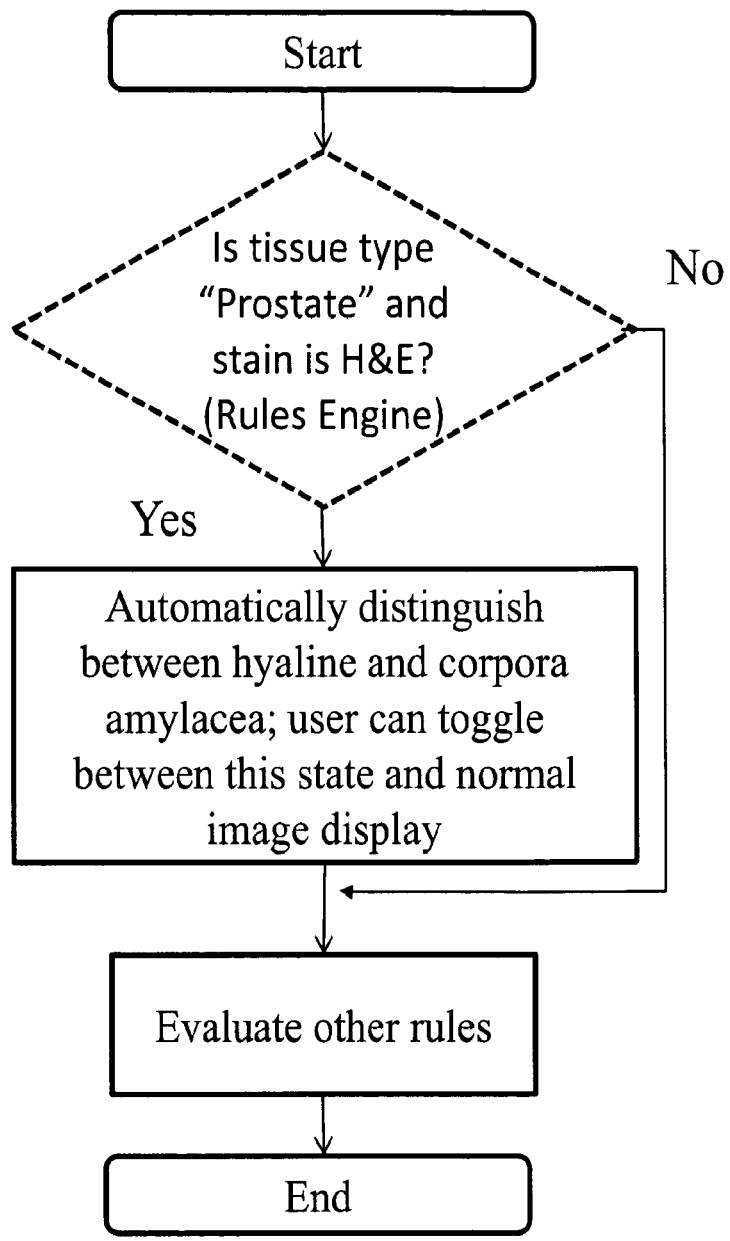
FIG. 5 illustrates a Readflow™ for GU (Prostate Hyaline, Corpora amylacea) in accordance with an embodiment of the present invention.
Figure 5A:
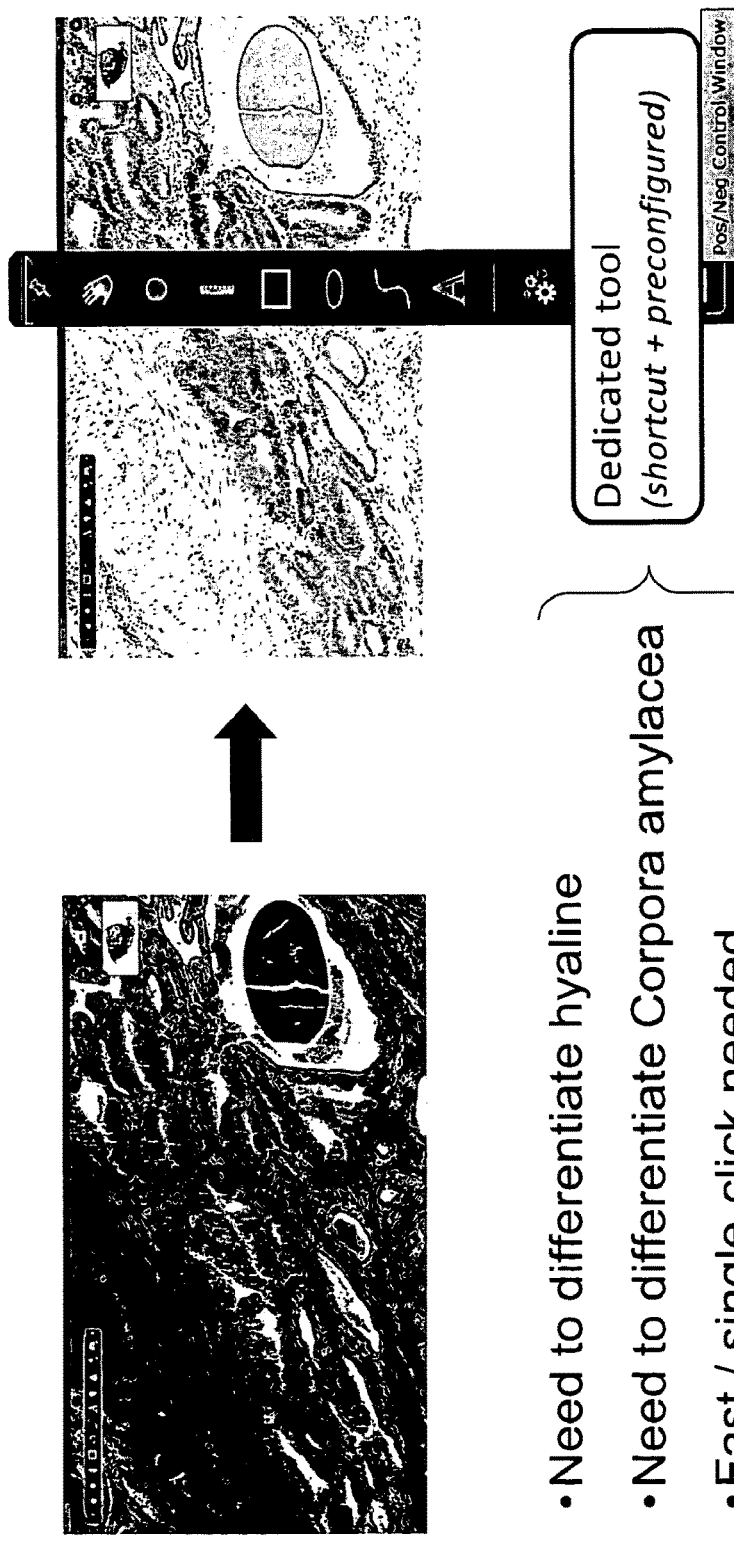
FIG. 5a demonstrates a user interface view of the Readflow™ illustrated in FIG. 5.

Referring to FIGS. 5 and 5a, for the GU (Prostate hyaline and corpora amylacea) Readflow™, when the slide is loaded and the tissue type is "prostate" and stain type is "H&E", the tool is automatically initialized to distinguish Hyaline and corpora amylacea. The pathologists may use a shortcut key or the like in association with the user interface as appreciated by one skilled in the art to quickly turn on and off this display mode.

GU (Prostate Tumor Area) Readflow™

Figure 6:
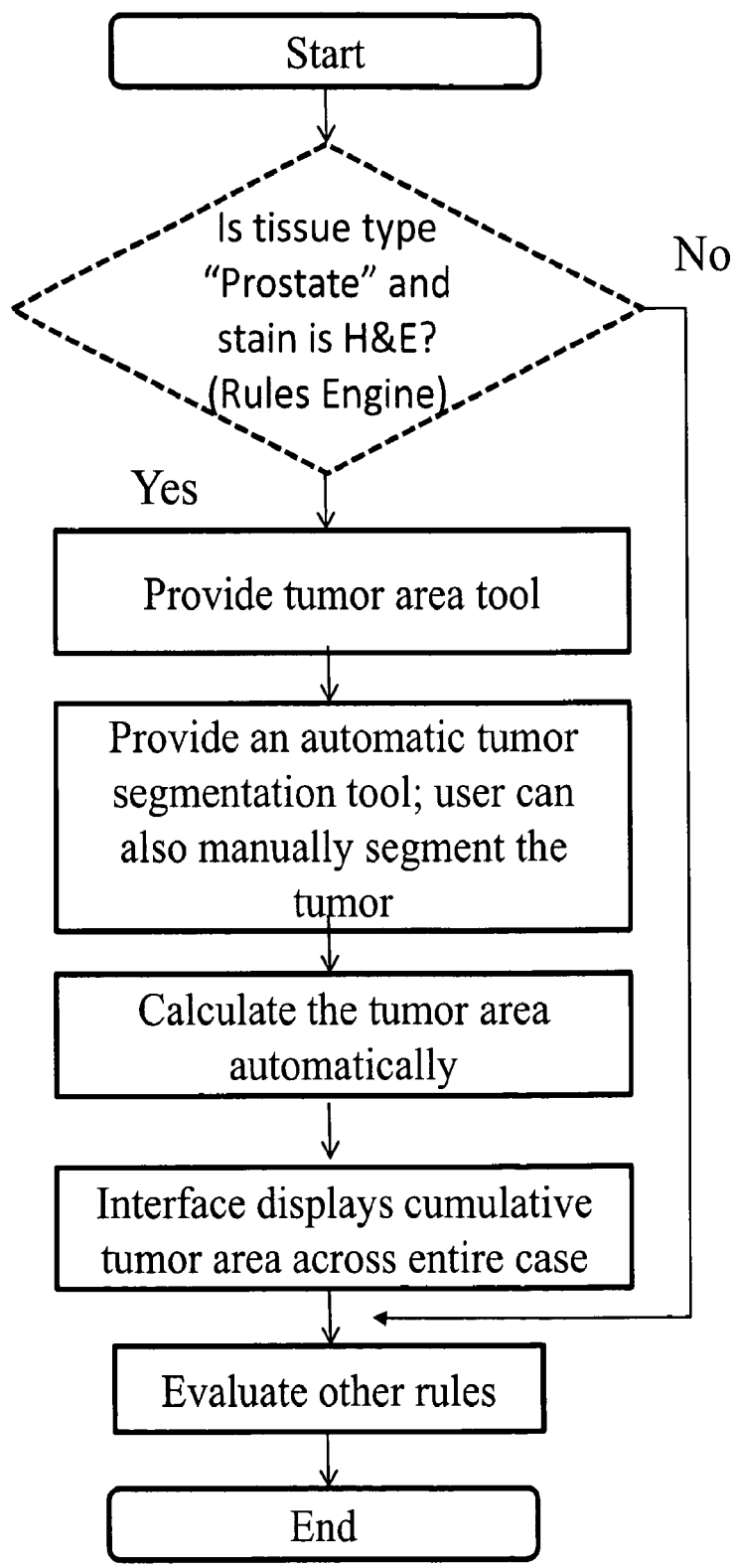
FIG. 6 illustrates a Readflow™ for GU (Prostate tumor ar) in accordance with an embodiment of the present invention.
Figure 6A:
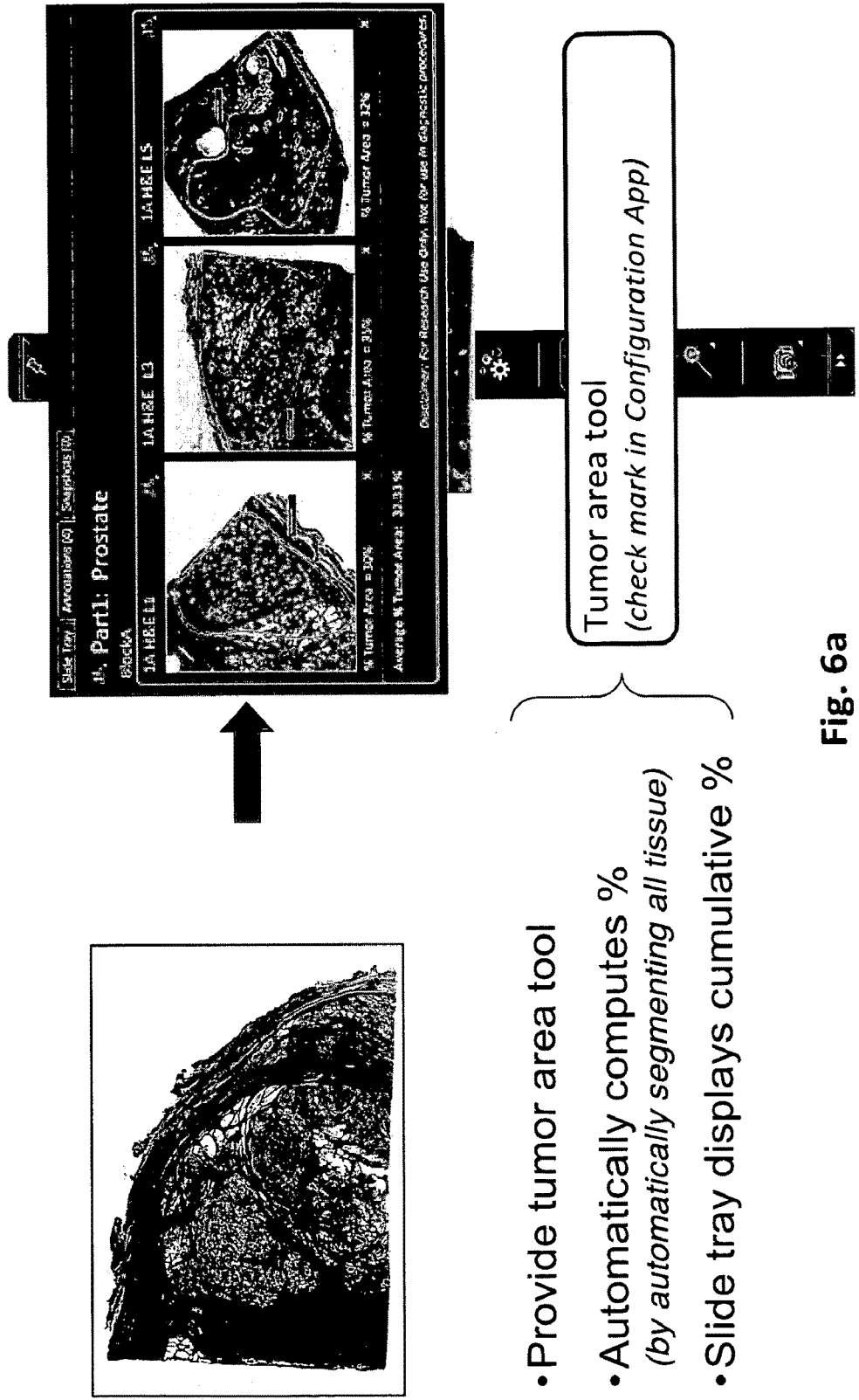
FIG. 6a demonstrates a user interface view of the Readflow™ illustrated in FIG. 6.

As illustrated in FIGS. 6 and 6a, for the GU (prostate tumor area) Readflow™, when the slide is loaded and the tissue type is prostate and stain type is H&E, a tumor area calculation tool may be enabled. The pathologists can use this tool to mark a tumor region; the tool accumulates the tumor area across all the regions on the slide and case and displays that to the user. More importantly, the tool automatically finds the respective entire tumor area and displays a percent area of tumor for each slide as well as accumulated across all slides.

GU (Kidney, Cancer Near Margins) Readflow™

Figure 7:
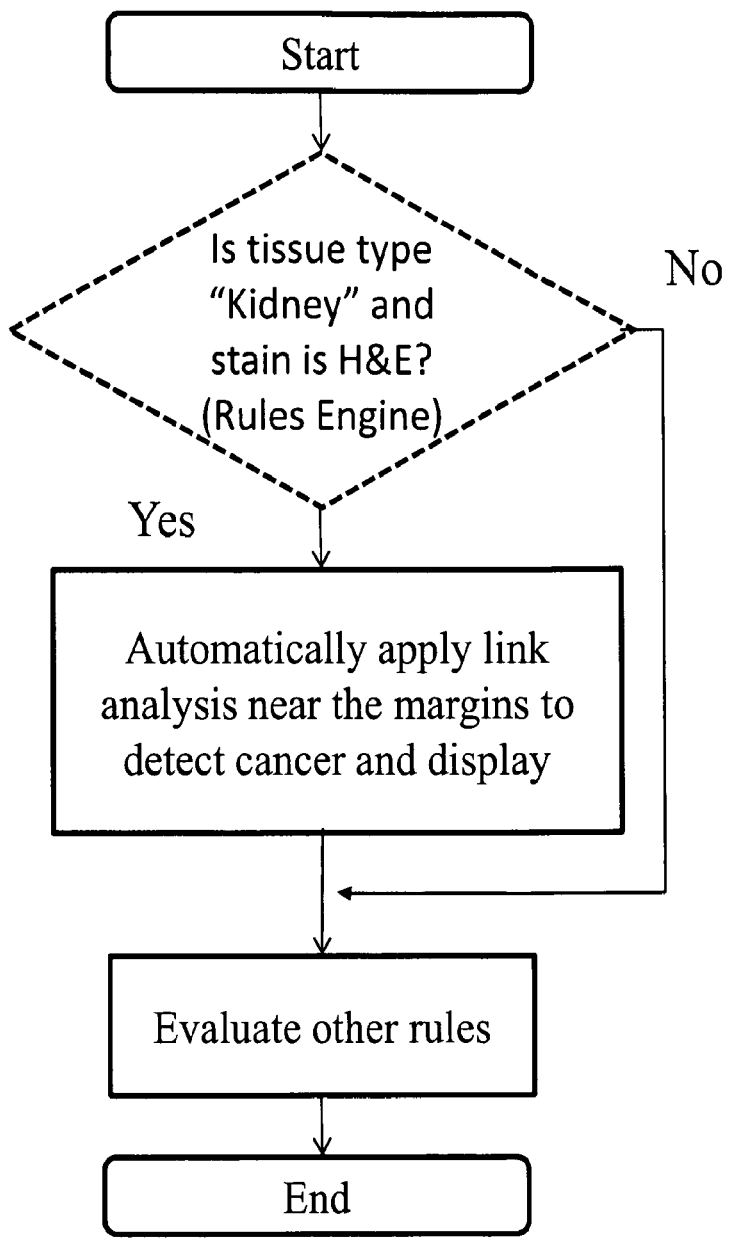
FIG. 7 illustrates a Readflow™ for Kidney (cancer near margins) in accordance with an embodiment of the present invention.
Figure 7A:
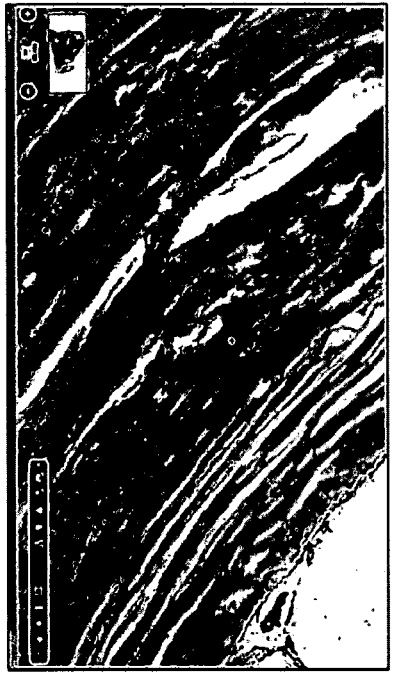
FIG. 7a demonstrates a user interface view of the Readflow™ illustrated in FIG. 7.
Figure 7A:
Figure 7A:

With respect to FIGS. 7 and 7a, for the GU (kidney, cancer near margins) Readflow™, when the slide is loaded and the tissue type is "kidney" and the stain type is "H&E", the ink analysis tool may be applied to identify the margins to enable localization of cancer near the margins.

GU (Kidney-Fuhrman) Readflow™

Figure 8:
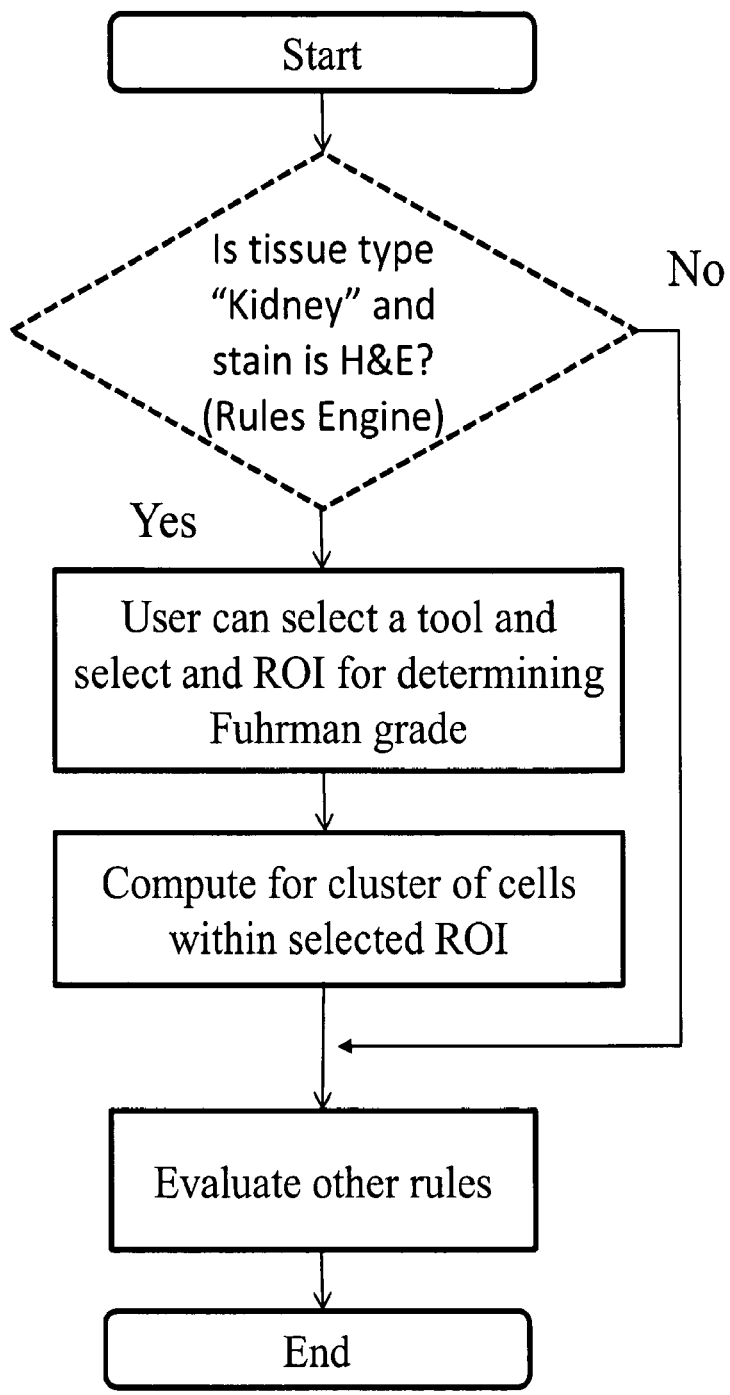
FIG. 8 illustrates a Readflow™ for Kidney-Fuhrman Grade in accordance with an embodiment of the present invention.
Figure 8A:
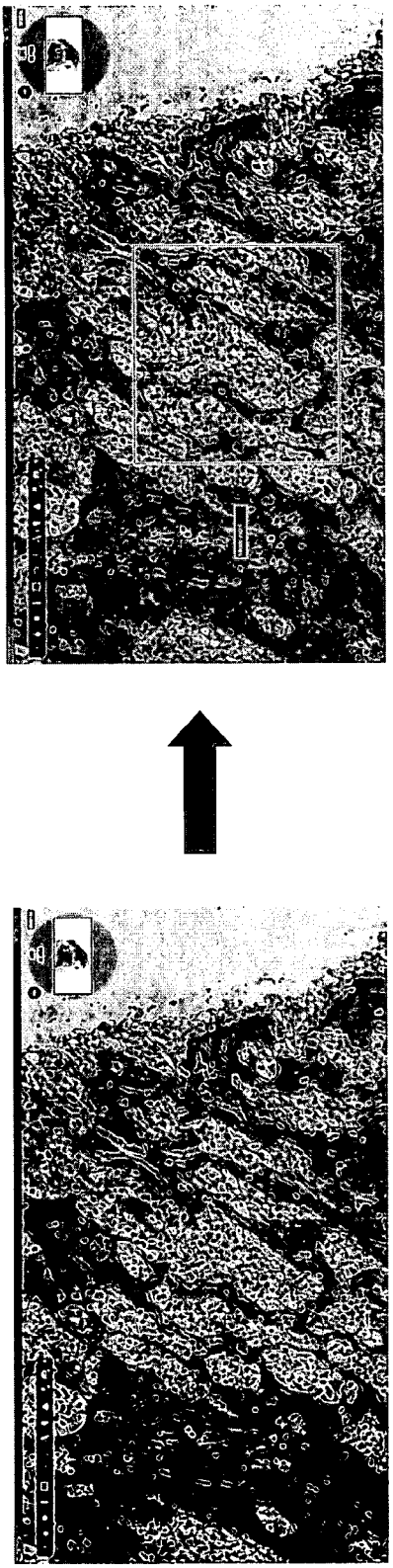
FIG. 8a demonstrates a user interface view of the Readflow™ illustrated in FIG. 8.

As illustrated in FIGS. 8 and 8a, for the GU (kidney-Fuhrman) Readflow™, when the slide is loaded and the tissue type is "kidney" and the stain type is "H&E", in addition to the ink analysis tool, a Furman grading tool may also be enabled. The pathologists may use this tool to mark out a region on the slide and the tool calculates the Fuhrman grade and presents the results to the user.

Tissue Jumper Readflow™

Figure 9:
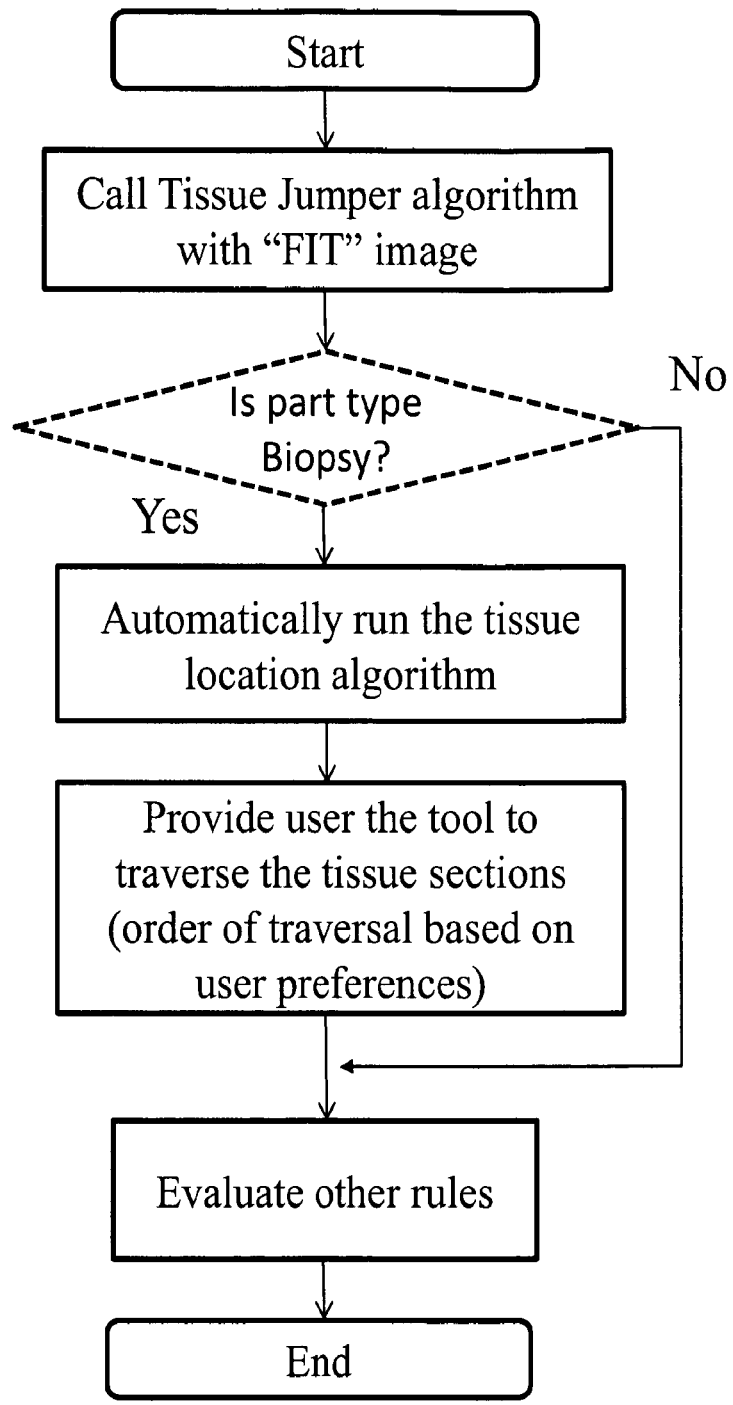
FIG. 9 illustrates a Readflow™ for Tissue Jumper in accordance with an embodiment of the present invention.
Figure 9A:
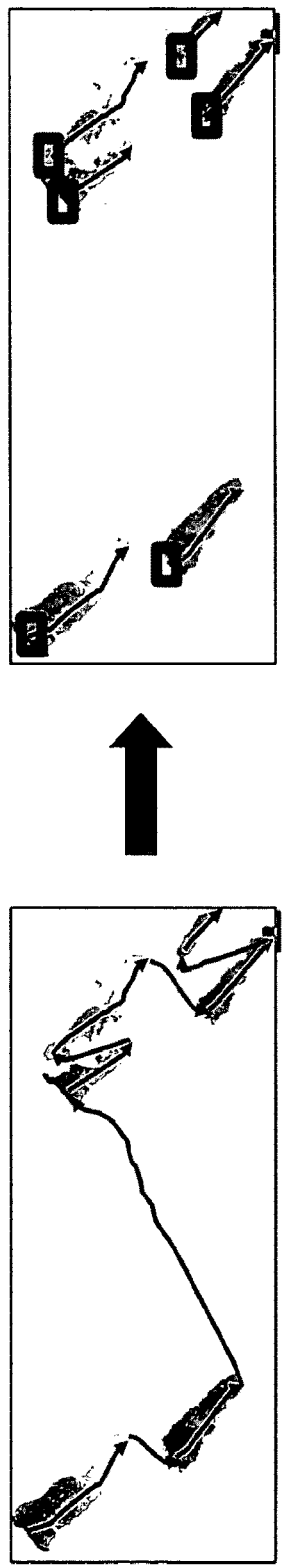
FIG. 9a demonstrates a user interface view of the Readflow™ illustrated in FIG. 9.

For the tissue jumper Readflow™, as demonstrated in FIGS. 9 and 9a, when the slide is loaded and the procedure type is biopsy, an algorithm may be executed to detect the different tissue sections on the slide. The algorithm orders the tissue based on user preferences. The user may automatically traverse between the different tissues using a keyboard shortcut or an input device. The order of traversal and field of view position for each tissue may be based on user preferences. The Tissue jumper Readflow™ may not be restricted to just the currently open slide; the tissue jumper may be extended to jump to the same tissue section across different slides in the same case. This feature extension would be available as part of the user preferences settings.

Skin (Melanoma) Readflow™

Figure 10:
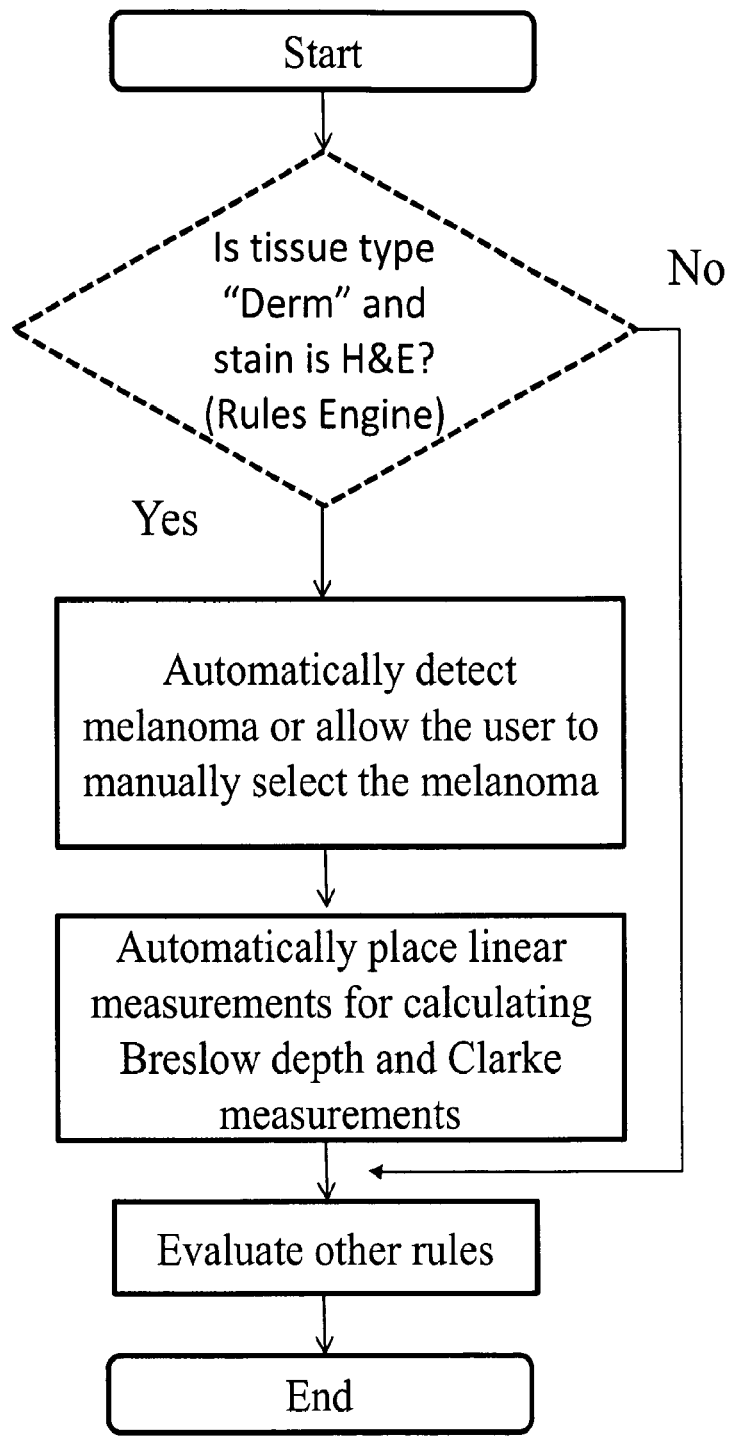
FIG. 10 illustrates a Readflow™ for Derm (H&E) Melanoma in accordance with an embodiment of the present invention.

Referring to FIG. 10, for the skin (melanoma) Readflow™, when the slide is loaded and the tissue type is "skin" or "derm" and the stain type is "H&E", a melanoma detection tool may be enabled. This tool locates a melanoma in the slide and places the Breslow and Clark calculation measurements on the melanoma for the pathologist. Alternatively, the tool can be configured to permit the user to select a melanoma.

Figure 10A:
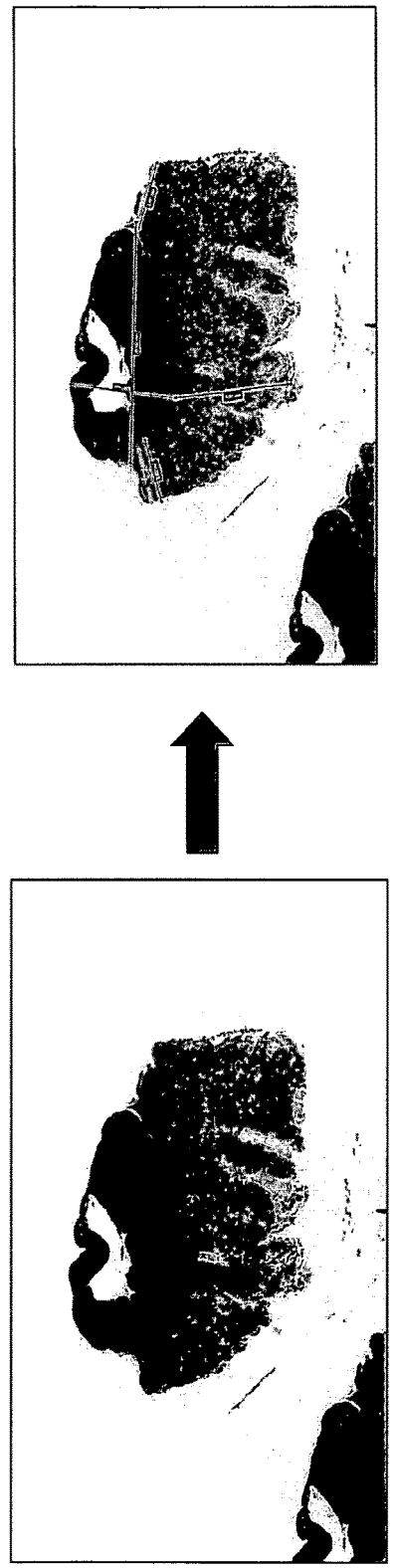
FIG. 10a demonstrates a user interface view of the Readflow™ illustrated in FIG. 10.

With respect to FIG. 10a, it can be seen that a hanging protocol associated with this type of tissue type can be applied such that, for example, the digital slides are automatically presented to the pathologist horizontally and at a 5× magnification, in addition to providing the melanoma detection tool in the user interface as discussed previously.

Skin (Epidermis Alignment) Readflow™

Figure 11:
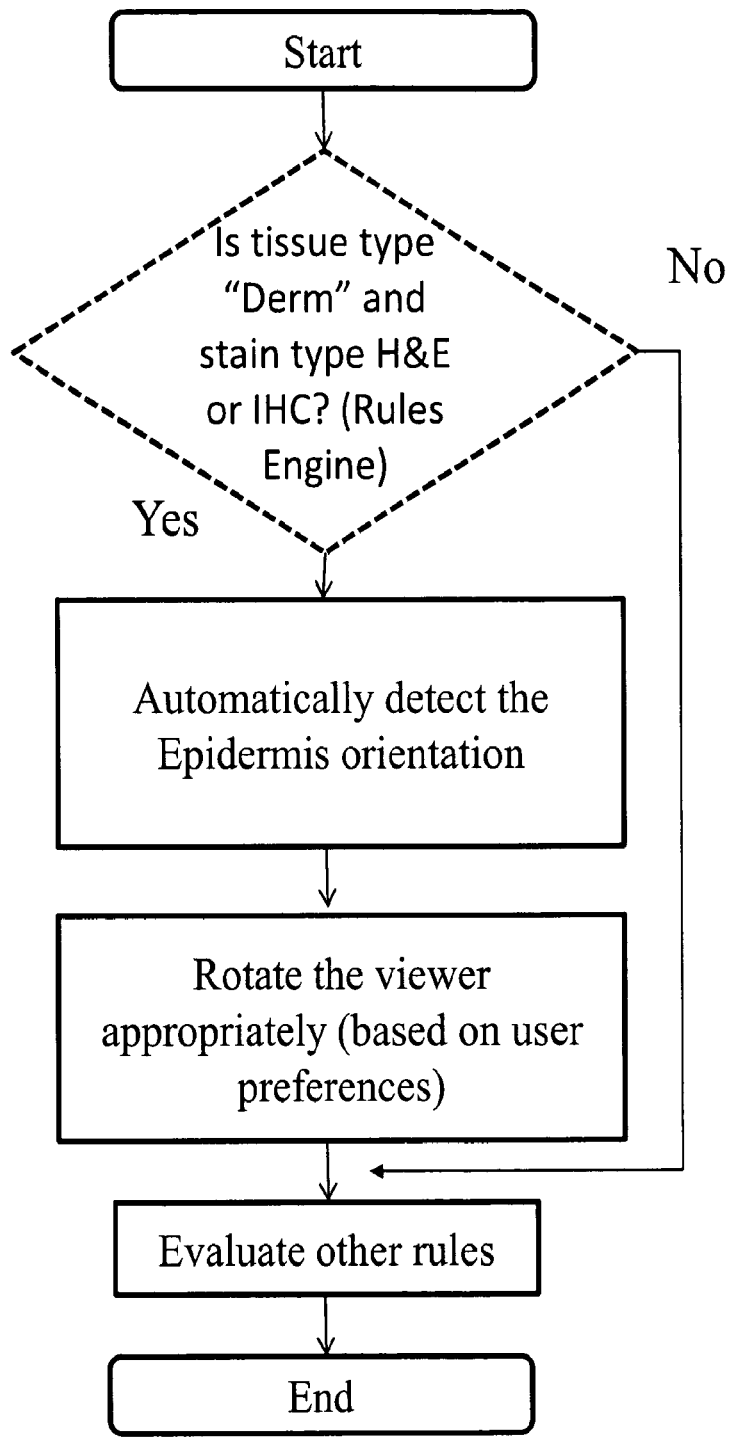
FIG. 11 illustrates a Readflow™ for Derm (H&E, IHC) Epidermis alignment in accordance with an embodiment of the present invention.

In relation to FIG. 11, for the skin (Epidermis alignment) Readflow™, when the slide contains the tissue type "skin" and the stain type is "H&E" or "IHC", the rules engine may cause an epidermis detection algorithm may be launched. The slide containing the epidermis is aligned based on the user preferences, for example, Epidermis on top/Dermis on bottom. Furthermore, the orientation of the slide containing epidermis may be altered based on user preferences, if any have been provided.

Breast (H&E Biopsy+IHC) Readflow™

Both normal and diseased cells have certain physical characteristics that can be used to differentiate them. These characteristics include complex patterns, rare events, and subtle variations in color and intensity, which are what the pathologist looks for when reviewing.

Hematoxilin and Eosin (H&E) is a method of staining that is used to study the morphology of tissue samples. Oncologists attempt to identify particular types of cancer by detecting variations in the patterns from the normal tissue. H&E staining can also be used to determine the pathological grading/staging of cancer (e.g. the Richardson and Bloom Method).

This pathological grading of cancer is important from both a diagnostic and predictive perspective. Currently, pathologists must rely on manually analyzed samples without the benefit of, for example, a software tool and/or reproducibility results with minimal variations.

Figure 12:
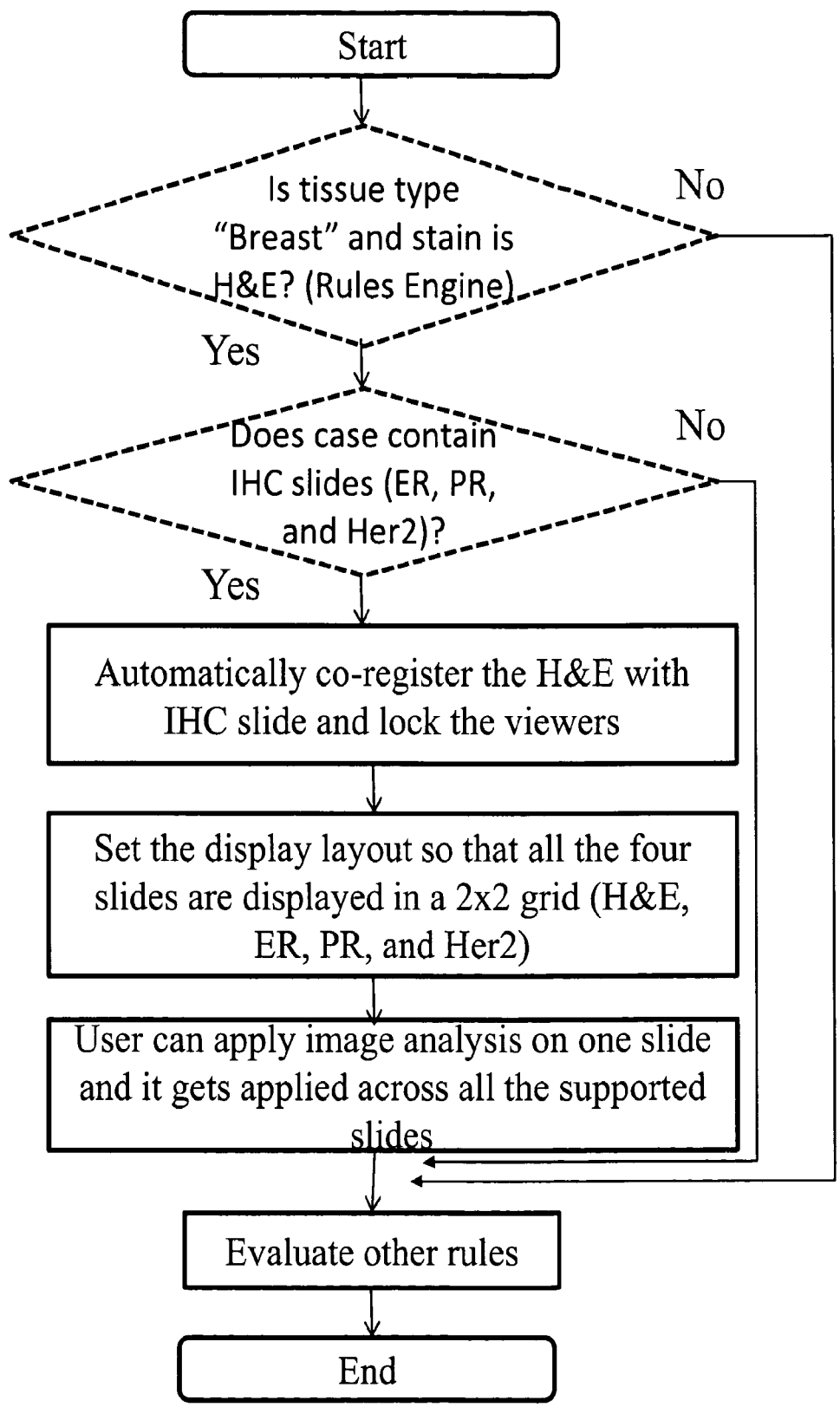
FIG. 12 illustrates a Readflow™ for Breast Biopsy +IHC slides in accordance with an embodiment of the present invention.

Referring, now, to FIG. 12, the breast (H&E biopsy and IHC) Readflow™ eliminates the current problems with reading these samples. When the slide is loaded and the tissue type is "Breast" and the stain type is "H&E" and the case panel contains other IHC slides (ER, PR, Hercept), the slides are all co-registered and locked. The interface displays a multitude of slides (H&E, ER, PR, Hercept, Ki-67, negative control and positive control) in any combination in a 2×2 grid (based on user preferences). The user may either apply annotations to the H&E slide which then get applied across the other IHC slides or the user may run IHC image analysis on all the IHC slides with a single click instead of having to pick the appropriate algorithm in each view (done automatically by the Readflow™). The co-registration may also happen using the pre-processing engine.

Breast Biopsy Readflow™ (Control Tissue)

Figure 13:
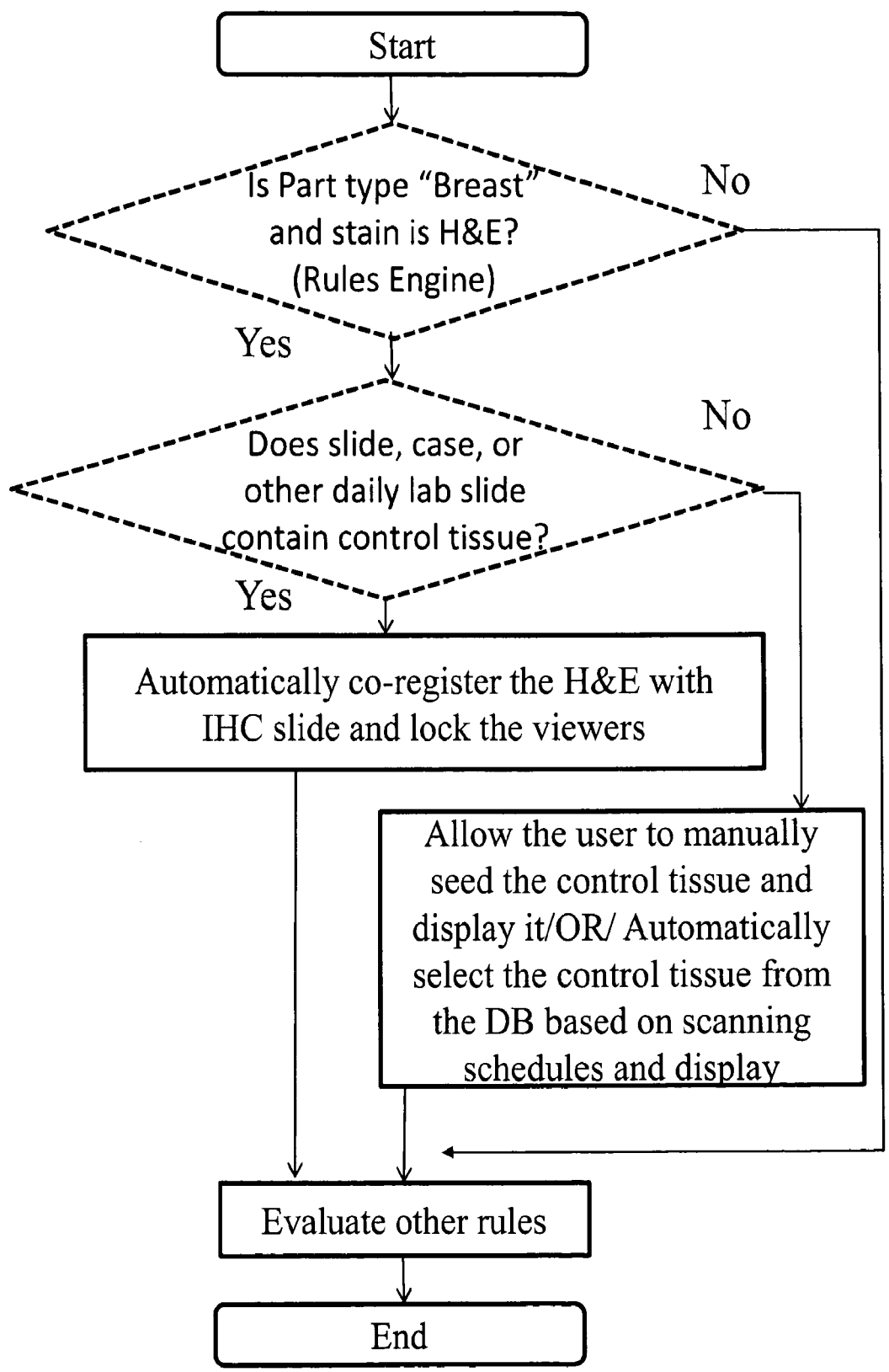
FIG. 13 illustrates a Readflow™ for Breast Biopsy (Control Tissue) in accordance with an embodiment of the present invention.

With respect to FIGS. 13 and 13a, for the breast (H&E, IHC+control tissue) Readflow™, when the slide is loaded and the tissue type is "Breast" and the stain type is one of the IHC markers (ER, PR, Her2, KI-67, or other) and a site-specific configuration flag is being set, a control tissue detection algorithm may be enabled to find control tissue on the same slide, the slide in the panel that contains control tissue, or the daily or less frequent control tissue slide generated in the lab. If the control tissue detection algorithm detects a control tissue, it selects a region of interest from within the control tissue and displays that on the interface. If the control tissue algorithm doesn't automatically detect a control tissue, a manual control tissue selection tool may be enabled. This tool allows the user to select a Region of interest from the control tissue to be displayed on the interface.

Breast Core Biopsy Readflow™

Figure 14:
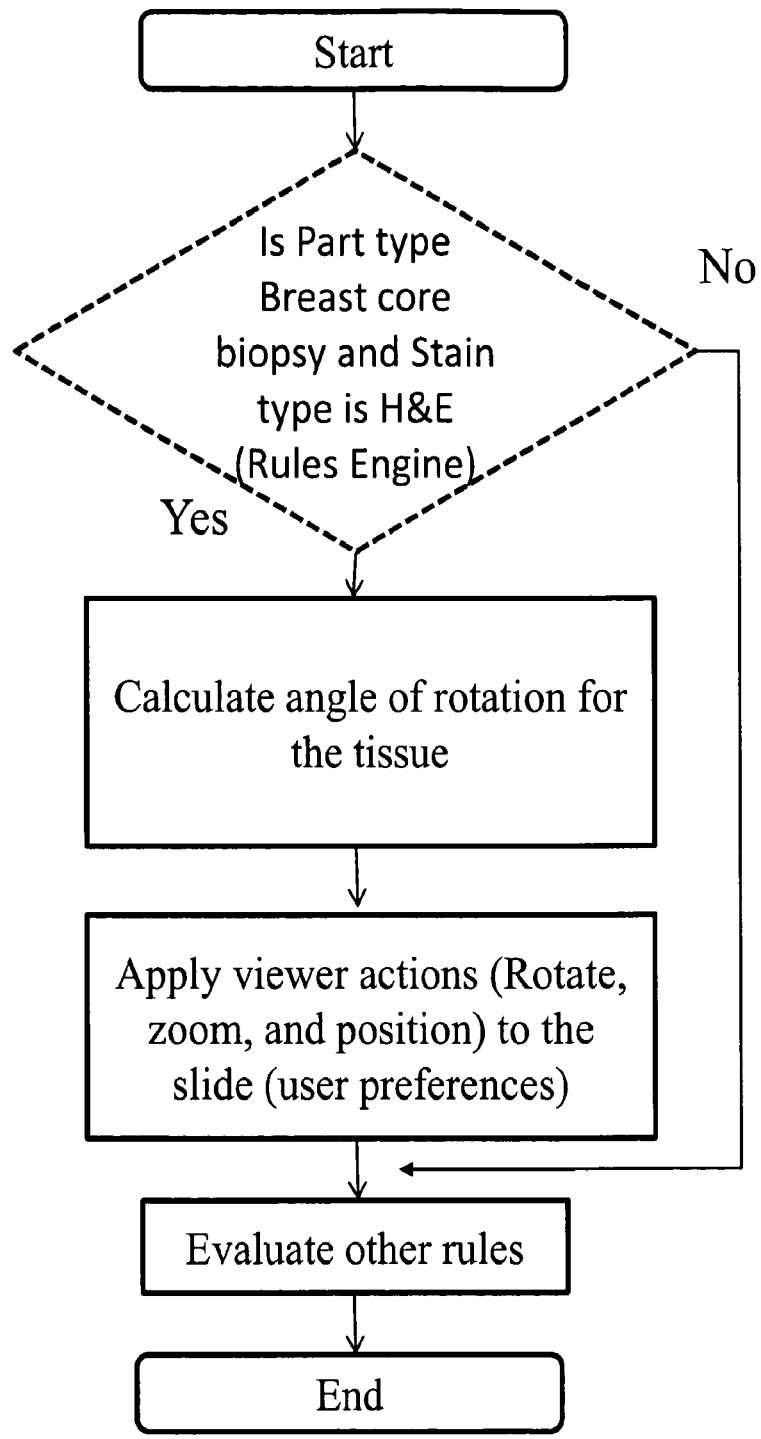
FIG. 14 illustrates a Readflow™ for Breast Core Biopsy in accordance with an embodiment of the present invention.
Figure 14A:
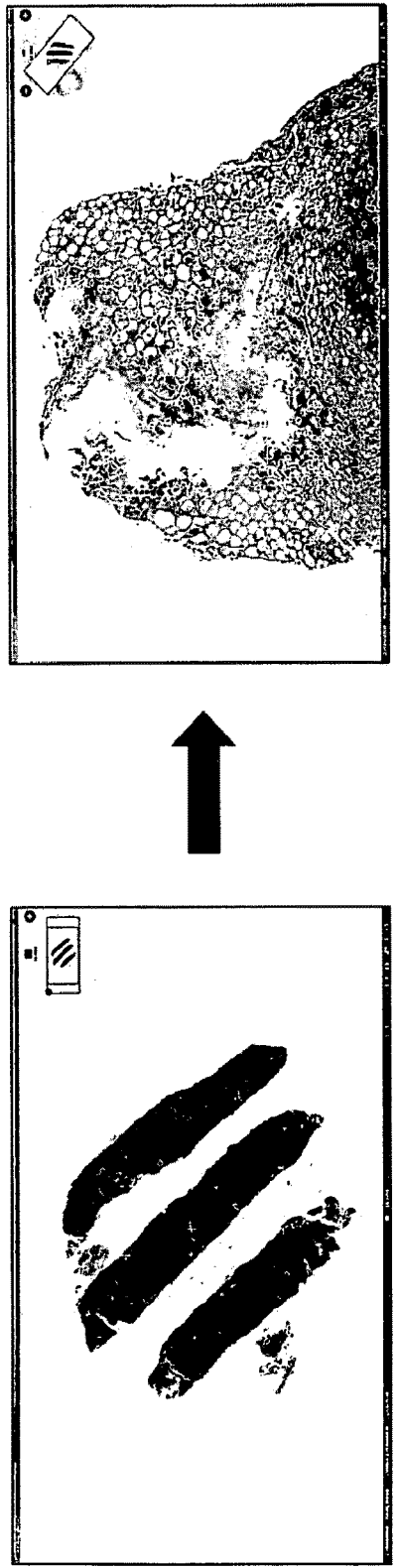
FIG. 14a demonstrates a user interface view of the Readflow™ illustrated in FIG. 14.

With reference, now, to FIGS. 14 and 14a, for the breast core biopsy (H&E/IHC) Readflow™, when the slide is loaded and the tissue type is "Breast" and the stain type is either "H&E" or one of the IHC stains, an algorithm is applied to detect the angle of inclination for the slide and the entire slide is oriented either vertically, horizontally or whatever user preference is chosen. The slide is also set to a lower magnification (i.e. 10×, 5× etc. based on chosen user preference) and the initial field of view is to the left top position of the left most tissue, or whatever was chosen in the user preferences. The orientation angle calculation could be done using the pre-processing engine.

The invention described herein has a number of advantages and benefits. For example, the systems and methods discussed herein allow for the optimization and efficiency in the interaction between pathologists and the digital pathology images. Additionally, the systems and methods can be customized to an individual user's preference as well as customized to a facility's preference, allowing for even more flexibility and productivity in reading digital pathology images.

While the present invention has been described in terms of its presently preferred embodiments, it will be apparent to those skilled in the art that various changes can be made to the disclosed embodiments without departing from the scope of the invention as defined by the following claims.

What is claimed is:

1. A system for displaying digital pathology images that facilitates evaluation on a graphical user interface comprising:
    a scanner configured to capture digital pathology images;
    at least one information management system, the at least one information management system configured to acquire and transmit data, wherein the data comprises the digital pathology images, associated case information, case or procedure type and/or user preferences;
    a processor, the processor configured to evaluate the data from the at least one information management system based on at least one or more of case type and procedure type, and generating based on the evaluated data at least one of modified digital images and a modified user interface, wherein the at least one of modified digital images and a modified user interface comprises one or more of changed image orientation, changed image magnification, changed image display area, highlighting a tissue feature of interest, and displaying specialized analysis tools specific to a disease type or tissue type;
    the processor further configured to implement a rules engine to evaluate the digital pathology images based on predefined rules for each case type, the predefined rules comprising one or more of guidelines of governing bodies, hanging protocols, test-specific rules, case-type specific rules, user preference, and institution preference;
    a pre-processing engine to process the data prior to display on the user interface, wherein the data is subjected to at least one of algorithms and co-registration to obtain output data that is used to create at least one of the modified digital images and modified user interface; and a workstation comprising a display device and an input component, wherein the display device displays at least one of the modified digital images and a modified user interface.

2. The system of claim 1, wherein the at least one information management system is selected from a group, including: a digital library, a database, a user management system, a case management system, an image management system, a rules management system, a laboratory information management system, an electronic medical record.

3. The system of claim 2, wherein the image management system manages at least digital images.

4. The system of claim 2, wherein the case management system manages at least case information.

5. The system of claim 2, wherein the user management system manages information about a user's preferences.

6. The system of claim 1, wherein the digital image data is categorized and organized based on the user preferences and/or case information, wherein the digital image data, user preferences and case information are acquired from at least one information management system.

7. The system of claim 1, wherein the rules engine comprises a set of predefined rules for each user preference, the user preference being determined by the user management system.

8. The system of claim 7, wherein the rules engine determines the user preference based on previous behaviors of the user.

9. The system of claim 1, wherein the processor modifies the behavior of the user interface by providing user interface tools that can alter the appearance of the user interface, wherein the tools provided are based on one or more of the case information and user's preferences.

10. A method for displaying digital pathology images that facilitates evaluation on a graphical user interface, the method, comprising:
capturing original digital pathology images using a scanner;
acquiring data, using a processor, wherein the acquired data comprises one or more of the original digital pathology images, associated case information, user preferences, and case or procedure type;
   applying a rule set to the data based on at least one or more of case type and procedure type;
   generating based on the applied rule set at least one of modified digital images and a modified user interface, wherein the at least one of modified digital images and a modified user interface comprises one or more of changed image orientation, changed image magnification, changed image display area, highlighting a tissue feature of interest, and displaying specialized analysis tools specific to a disease type or tissue type;
   applying a rules engine to the data, the rules engine evaluating the data based on predefined rules for each case type, the predefined rules comprising one or more of guidelines of governing bodies, hanging protocols, test-specific rules, case-type specific rules, user preference, and institution preference;
   processing the data prior to display on the user interface, wherein the data is subjected to at least one of algorithms and co-registration to obtain output data that is used to create at least one of the modified digital images and modified user interface;
   creating at least one of the modified digital images and modified user interface; and
   displaying at least one of the modified digital pathology images and the modified user interface.

11. The method of claim 10, wherein the digital images are associated with case information based on the parameters entered by users, and the digital images are organized and grouped by the associated case information.

12. A non-transitory computer-readable storage medium including a set of instructions for a computer for displaying digital pathology images that facilitates evaluation on a graphical user interface, the set of instructions comprising:
   at least one information management system, the at least one information management system configured to acquire and transmit data, wherein the data comprises digital pathology images, associated case information, case or procedure type and/or user preferences;
   at least one rule set to be applied to the data based at least on one or more of case type and procedure type, the rules set configured to generate at least one of modified digital images and a modified user interface, wherein the at least one of modified digital images and a modified user interface comprises one or more of changed image orientation, changed image magnification, changed image display area, highlighting a tissue feature of interest, and displaying specialized analysis tools specific to a disease type or tissue type;
   at least one rules engine, the at least one rules engine configured to evaluate the data based on predefined rules for each case type, the predefined rules comprising one or more of guidelines of governing bodies, hanging protocols, test-specific rules, case-type specific rules, user preference, and institution preference;
   at least one pre-processing engine configured to process the data prior to display on the user interface, wherein the data is subjected to at least one of algorithms and co-registration to obtain output data that is used to create at least one of the modified digital images and modified user interface;
   whereby at least one of the modified digital images and the modified user interface is displayed.

* * * * *